US012790457B2

(12) United States Patent
Matsubara et al.

(10) Patent No.: US 12,790,457 B2
(45) Date of Patent: Nov. 10, 2026

(54) MONOMER PRODUCTION SYSTEM AND MONOMER PRODUCTION METHOD

(71) Applicant: MITSUBISHI HEAVY INDUSTRIES, LTD., Tokyo (JP)

(72) Inventors: Wataru Matsubara, Tokyo (JP); Yoshio Seiki, Tokyo (JP); Minoru Genta, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 524 days.

(21) Appl. No.: 18/564,919

(22) PCT Filed: Feb. 18, 2022

(86) PCT No.: PCT/JP2022/006713
§ 371 (c)(1),
(2) Date: Nov. 28, 2023

(87) PCT Pub. No.: WO2022/254814
PCT Pub. Date: Dec. 8, 2022

(65) Prior Publication Data

US 2024/0262976 A1 Aug. 8, 2024

(30) Foreign Application Priority Data

May 31, 2021 (JP) ................................ 2021-091775

(51) Int. Cl.
*C08J 11/24* (2006.01)
*B01D 3/14* (2006.01)
(Continued)

(52) U.S. Cl.
CPC ............... *C08J 11/24* (2013.01); *B01D 3/143* (2013.01); *B01J 19/0006* (2013.01);
(Continued)

(58) Field of Classification Search
CPC ..... C07C 29/1285; C07C 51/09; C07C 67/08; C07C 29/128; C07C 69/82; B01J 19/0006;
(Continued)

(56) References Cited

U.S. PATENT DOCUMENTS

| | | |
|---|---|---|
| 3,907,868 A | 9/1975 | Currie et al. |
| 5,576,456 A | 11/1996 | Gamble et al. |

FOREIGN PATENT DOCUMENTS

| | | |
|---|---|---|
| JP | 2002-114722 A | 4/2002 |
| JP | 2003-49020 A | 2/2003 |

(Continued)

OTHER PUBLICATIONS

International Search Report and Written Opinion of the International Searching Authority for International Application No. PCT/JP2022/006713, dated Apr. 26, 2022, with English translation.

(Continued)

*Primary Examiner* — Jafar F Parsa
(74) *Attorney, Agent, or Firm* — Birch, Stewart, Kolasch & Birch, LLP

(57) ABSTRACT

To improve yield of monomers. A monomer production system includes a dissolving unit that stores therein a polyester solution, a first reaction unit into which the polyester solution and a reaction solvent are introduced and that depolymerizes the polyester in the polyester solution and extracts a first depolymerized polyester containing the depolymerized polyester into the reaction solvent, a second reaction unit that further depolymerizes the first depolymerized polyester and generates a second depolymerized polyester that is the further depolymerized first depolymerized polyester, a separation unit that separates the reaction solvent in which the second depolymerized polyester is dissolved into the reaction solvent, a carboxylic acid-derived (Continued)

monomer, an alcohol component monomer, and residual substances that are components other than the reaction solvent, the carboxylic acid-derived monomer, and the alcohol component monomer, and contain oligomers, and inlet pipes that introduce the carboxylic acid-derived monomer and the residual substances into the dissolving unit.

12 Claims, 7 Drawing Sheets

(51) Int. Cl.
*B01J 19/00* (2006.01)
*B01J 19/24* (2006.01)
*C07C 29/128* (2006.01)
*C07C 51/09* (2006.01)

(52) U.S. Cl.
CPC ......... *B01J 19/245* (2013.01); *C07C 29/1285* (2013.01); *C07C 51/09* (2013.01); *B01J 2219/0004* (2013.01); *B01J 2219/00184* (2013.01); *C08J 2367/02* (2013.01)

(58) Field of Classification Search
CPC .............. B01J 19/245; B01J 2219/0004; B01J 2219/0184; B01J 2219/0006; B01D 3/143; C08J 11/24; C08J 2367/02
See application file for complete search history.

(56) References Cited

FOREIGN PATENT DOCUMENTS

| | | |
|---|---|---|
| JP | 2003-300915 A | 10/2003 |
| JP | 2005-289826 A | 10/2005 |
| JP | 4008214 B2 | 11/2007 |

OTHER PUBLICATIONS

Extended European Search Report for European Application No. 22815573.5, dated Mar. 14, 2025.

MONOMER PRODUCTION SYSTEM AND MONOMER PRODUCTION METHOD

FIELD

The present disclosure relates to a monomer production system and a monomer production method.

BACKGROUND

In recycling of polyester, attempts have been made to depolymerize the polyester into monomers, and then polymerize the monomers again. Patent Literature 1 describes a technology in which polyethylene terephthalate (PET) and dimethyl terephthalate (DMT) are mixed and dissolved, the PET is depolymerized by causing supercritical methanol to act in a first reaction unit, and the PET is monomerized into DMT and ethylene glycol (EG) by further causing the depolymerized PET to react with methanol in a second reaction unit.

CITATION LIST

Patent Literature

Patent Literature 1: Japanese Patent No. 4008214

SUMMARY

Technical Problem

When recycling the polyester as described above, the yield of the monomers is required to be improved.

The present disclosure aims to solve the problem described above, and it is an object thereof to provide a monomer production system and a monomer production method capable of improving the yield of the monomers.

Solution to Problem

In order to solve the above problem and achieve the object, a monomer production system according to the present disclosure includes: a dissolving unit configured to store a polyester solution in which polyester is dissolved in a carboxylic acid-derived monomer; a first reaction unit into which the polyester solution and a reaction solvent to react with the polyester are introduced to bring the polyester solution into contact with the reaction solvent to depolymerize the polyester in the polyester solution and extract a first depolymerized polyester containing the depolymerized polyester into the reaction solvent; a second reaction unit into which the reaction solvent with the extracted first depolymerized polyester is introduced to cause the first depolymerized polyester to further react with the reaction solvent to further depolymerize the first depolymerized polyester and generate a second depolymerized polyester that is the further depolymerized first depolymerized polyester; a separation unit into which the reaction solvent with the dissolved second depolymerized polyester is introduced to separate the reaction solvent with the dissolved second depolymerized polyester into the reaction solvent, the carboxylic acid-derived monomer contained in the second depolymerized polyester, an alcohol component monomer contained in the second depolymerized polyester, and residual substances that are components other than the reaction solvent, the carboxylic acid-derived monomer, and the alcohol component monomer, the residual substances containing oligomers; and inlet pipes configured to introduce the carboxylic acid-derived monomer and the residual substances into the dissolving unit.

In order to solve the above problem and achieve the object, a monomer production method according to the present disclosure includes the steps of: generating a polyester solution in which polyester is dissolved in a carboxylic acid-derived monomer in a dissolving unit; depolymerizing the polyester in the polyester solution and extracting a first depolymerized polyester containing the depolymerized polyester into the reaction solvent by bringing the polyester solution into contact with the reaction solvent; further depolymerizing the first depolymerized polyester to generate a second depolymerized polyester that is the further depolymerized first depolymerized polyester by causing the first depolymerized polyester to further react with the reaction solvent; separating the reaction solvent with the dissolved second depolymerized polyester into the reaction solvent, the carboxylic acid-derived monomer contained in the second depolymerized polyester, an alcohol component monomer contained in the second depolymerized polyester, and residual substances that are components other than the reaction solvent, the carboxylic acid-derived monomer, and the alcohol component monomer, the residual substances containing oligomers; and introducing the carboxylic acid-derived monomer and the residual substances into the dissolving unit.

Advantageous Effects of Invention

According to the present disclosure, the yield of the monomers can be improved.

DESCRIPTION OF EMBODIMENTS

The following describes preferred embodiments of the present invention with reference to the accompanying drawings. The present invention is not limited by these embodiments, and when a plurality of embodiments are given, the present invention includes combinations of the embodiments.

First Embodiment

Recycling Process

Figure 1:
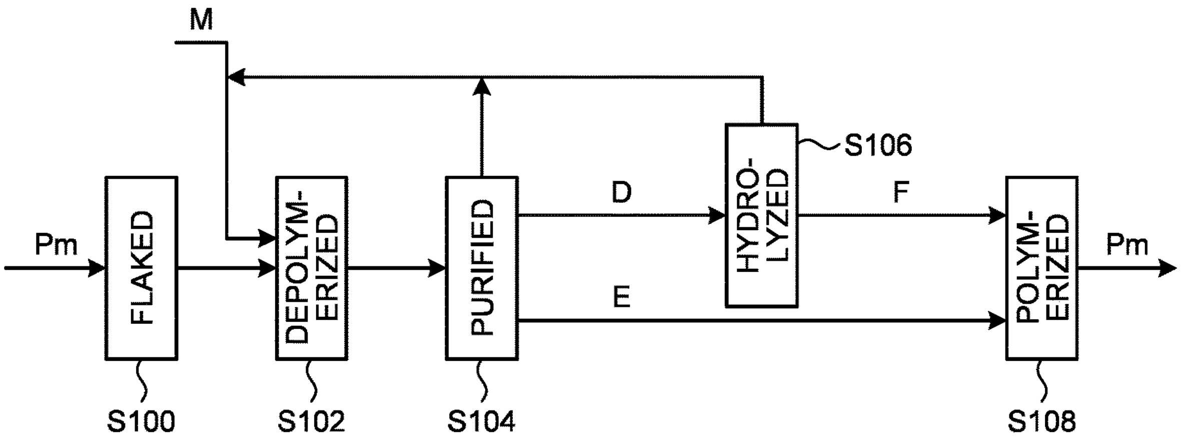
FIG. 1 is a schematic diagram of a polyester recycling process in an embodiment of the present invention.

FIG. 1 is a schematic diagram of a polyester recycling process in a first embodiment of the present invention. In the present embodiment, a process to recycle (regenerate) a polyester raw material Pm is performed by depolymerizing the polyester raw material Pm into monomers and polymerizing the monomers again. Specifically, as illustrated in FIG. 1, the polyester raw material Pm is flaked (Step S100), and mixed with a reaction solvent M to depolymerize the polyester raw material Pm (Step S102); the depolymerized polyester monomers are purified (separated) to generate a carboxylic acid-derived monomer D and an alcohol component monomer E (Step S104); the monomer D is hydrolyzed to separate the reaction solvent M produced as a byproduct (Step S106); and a monomer F generated by hydrolyzing the monomer D is polymerized with the monomer E (Step S108) to regenerate the polyester raw material Pm. A monomer production system 1 of the present embodiment may perform only the process to produce the monomers D and E illustrated at Steps S102 and S104 without performing the process to perform the re-polymerization as illustrated at Step S108. In the present embodiment, the monomer D generated by the depolymerization reaction and residual substances R are also added to the polyester raw material Pm during the depolymerization, which will be described later in detail.

Polyester

The polyester raw material Pm to be depolymerized in the present embodiment is a substance containing polyester, but is not limited to a substance containing only the polyester component, and may contain components (such as impurities) other than the polyester component. The polyester raw material Pm is not particularly limited, but examples thereof include waste products of, for example, polyethylene terephthalate (PET), polyethylene butylene terephthalate (PEBT), polybutylene terephthalate (PBT), polycyclohexane dimethyl terephthalate (PCT), polyethylene naphthalate (PEN), polybutylene naphthalate (PBN), and polycarbonate (PC). The most typical application example is regeneration of PET bottles. In addition, PET films typified by photographic films, PET tapes typified by magnetic tapes, PET fibers used as polyester fibers, cups, trays, PET sheets used for transparent packaging, and the like can also be processed.

Reaction Solvent

The reaction solvent M is a solvent that reacts with the polyester to depolymerize the polyester. The reaction solvent M may be, for example, at least one of methanol, ethanol, and ethylene glycol.

Carboxylic Acid-Derived Monomer

The carboxylic acid-derived monomer D is a monomer that has a carboxylic group generated by the depolymerization reaction of the polyester. The monomer D may be, for example, dimethyl carboxylate or diethyl carboxylate. Moreover, the monomer D is preferably a monomer of terephthalic acid, which may be dimethyl terephthalate (DMT), for example.

Alcohol Component Monomer

The alcohol component monomer E is an alcohol component monomer generated by the depolymerization reaction of the polyester. The monomer E may be, for example, a dihydroxy compound (dihydric alcohol), or may even be ethylene glycol (EG).

The following describes a case, as an example, where the polyester is PET, the reaction solvent M is methanol, the monomer D is DMT, and the monomer E is EG.

Monomer Production System

Figure 2:
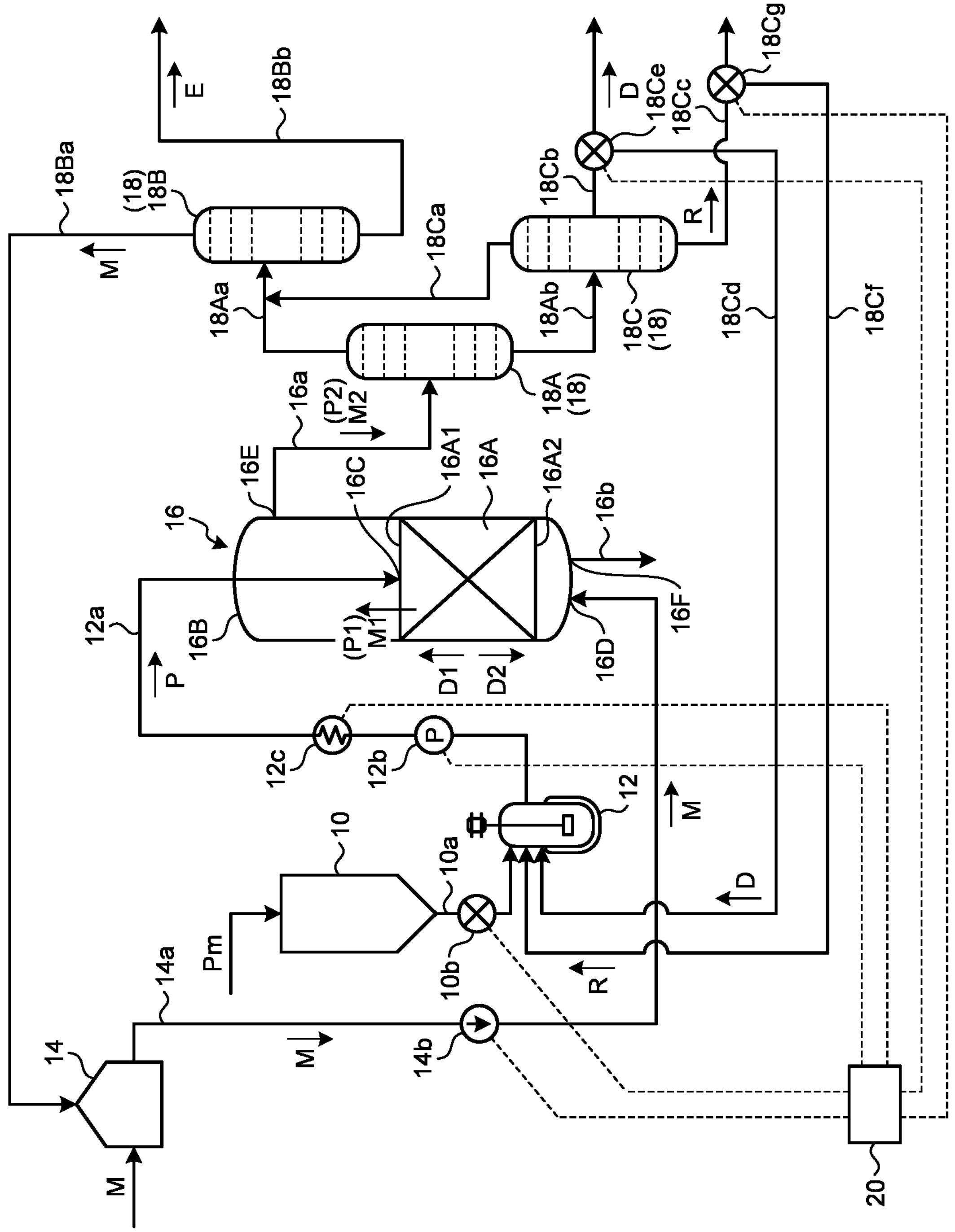
FIG. 2 is a schematic diagram of a monomer production system according to a first embodiment of the present invention.

FIG. 2 is a schematic diagram of the monomer production system according to the first embodiment. The monomer production system 1 according to the first embodiment is a system to generate the monomers D and E by monomerizing the polyester contained in the polyester raw material Pm. As illustrated in FIG. 2, the monomer production system 1 includes a storage unit 10, a dissolving unit 12, a solvent storage unit 14, a reaction unit 16 including a first reaction unit 16A and a second reaction unit 16B, a separation unit 18, and a control unit 20.

Storage Unit

The storage unit 10 is a tank (hopper) into which the polyester raw material Pm is introduced and stored. In the present embodiment, the flaked polyester raw material Pm is stored in the storage unit 10, but the polyester raw material Pm may have any shape and size. The storage unit 10 is connected to the dissolving unit 12 through an inlet pipe 10*a*. The polyester raw material Pm in the storage unit 10 is supplied to the dissolving unit 12 through the inlet pipe 10*a*. The inlet pipe 10*a* is provided with an adjusting unit 10*b* to adjust the amount of the polyester raw material Pm supplied from the storage unit 10 to the dissolving unit 12. The adjusting unit 10*b* is, for example, an on-off valve that supplies, when being open, the polyester raw material Pm in the storage unit 10 to the dissolving unit 12, and stops, when being closed, supplying the polyester raw material Pm in the storage unit 10 to the dissolving unit 12. The adjusting unit 10*b* is, however, not limited to being an on-off valve, but may be any mechanism capable of adjusting the supply of the polyester raw material Pm to the dissolving unit 12.

Dissolving Unit

The dissolving unit 12 is a tank that stores therein a polyester solution P in which the polyester contained in the polyester raw material Pm is dissolved in the monomer D. The monomer D and the polyester raw material Pm are supplied to the dissolving unit 12, and the polyester contained in the polyester raw material Pm is dissolved in the monomer D in the dissolving unit 12 to generate the polyester solution P. Dissolving the polyester in the monomer D in this way can reduce the viscosity to improve the fluidity, allowing the polyester to be easily led out to the reaction unit 16. Moreover, the dissolving unit 12 is also supplied with the residual substances R, which are to be described later, and in the dissolving unit 12, the polyester contained in the polyester raw material Pm is dissolved in the monomer D and oligomers contained in the residual substances R to generate the polyester solution P. That is, the polyester solution P can be said to be a solution in which the polyester is dissolved in the monomer D and the residual substances R. However, the present invention is not limited that the entire amount of the polyester is dissolved in the monomer D and the residual substances R in the polyester solution P, but at least a part of the polyester may be in the state of not being dissolved in the monomer D and the residual substances R.

The dissolving unit 12 is connected to the first reaction unit 16A, which is to be described later, through an inlet pipe 12*a*. The polyester solution P in the dissolving unit 12 is supplied to the first reaction unit 16A through the inlet pipe 12*a*. The inlet pipe 12*a* is provided with a supply unit 12*b* and a heating unit 12*c*. The supply unit 12*b* is a mechanism to supply the polyester solution P in the dissolving unit 12 to the first reaction unit 16A, and is a pump in the present embodiment. The heating unit 12*c* is a mechanism to heat the polyester solution P.

Solvent Storage Unit

The solvent storage unit 14 is a tank into which the reaction solvent M is introduced and stored. The solvent storage unit 14 is connected to the reaction unit 16 through an inlet pipe 14*a*. The reaction solvent M in the solvent storage unit 14 is supplied to the reaction unit 16 through the inlet pipe 14*a*. In more detail, the inlet pipe 14*a* is provided with a heating/pressurizing unit 14*b* that pressurizes and heats the reaction solvent M. The heating/pressurizing unit 14*b* pressurizes and heats the reaction solvent M to bring the reaction solvent M into a supercritical state or a subcritical state (a pressurized gas or a pressurized liquid). The reaction unit 16 is supplied with the reaction solvent M in the supercritical state or the subcritical state (the pressurized gas or the pressurized liquid).

Reaction Unit

The reaction unit 16 is a vessel into which the polyester solution P and the reaction solvent M are supplied. The reaction unit 16 includes the first reaction unit 16A and the second reaction unit 16B.

First Reaction Unit

The first reaction unit 16A is formed in the reaction unit 16. In the present embodiment, the first reaction unit 16A can be said to be a portion filled with a filling material in the reaction unit 16. As the filling material in the first reaction unit 16A, known filling materials used in gas-liquid or liquid-liquid contact devices can be used. For example, the same material as a filling material used in contact devices that extract active ingredients by bringing heavy oil in contact with water. Specific examples of the filling material include pipes made of, for example, stainless steel (SUS), Raschig rings, Berl saddles, and Tellerettes.

The inlet pipe 12*a* is connected to the first reaction unit 16A. In more detail, an inlet port 16C that is an opening of the inlet pipe 12*a* through which the polyester solution P is introduced from the dissolving unit 12 is connected to the first reaction unit 16A. The inlet port 16C is connected to a surface 16A1 on a first direction D1 side of the first reaction unit 16A. The inlet pipe 12*a* is connected to the surface 16A1 such that the inlet port 16C opens toward a second direction D2 opposite the first direction D1. Thus, in the present embodiment, the inlet port 16C opening toward the second direction D2 is connected to the surface 16A1 of the first reaction unit 16A, but is not limited to being connected in that way. For example, the inlet port 16C need not be directly connected to the first reaction unit 16A, but the inlet port 16C opening toward the second direction D2 may be connected to a portion on the first direction D1 side of the surface 16A1 of the first reaction unit 16A in the reaction unit 16.

The inlet pipe 14*a* is connected to the reaction unit 16. In more detail, an inlet port 16D that is an opening of the inlet pipe 14*a* through which the reaction solvent M is introduced from the solvent storage unit 14 is connected to the reaction unit 16. The inlet port 16D is connected to the second direction D2 side of a surface 16A2 on the second direction D2 side of the first reaction unit 16A. The inlet port 16D of the inlet pipe 14*a* is connected to a portion on the second direction D2 side of the surface 16A2 so as to open toward the first direction D1 or from a side surface toward the center. Thus, in the present embodiment, the inlet port 16D opening toward the first direction D1 or from the side surface toward the center is connected to a portion on the second direction D2 side of the surface 16A2 of the first reaction unit 16A, but is not limited to being connected in that way. For example, the inlet port 16D may be directly connected to the first reaction unit 16A, or may be connected to the surface 16A2 of the first reaction unit 16A.

Thus, in the present embodiment, the inlet port 16C through which the polyester solution P is introduced opens toward the second direction D2, and the inlet port 16D through which the reaction solvent M is introduced opens toward the first direction D1, or from the side surface toward the center. Accordingly, the polyester solution P and the reaction solvent M are introduced into the first reaction unit 16A in directions toward each other.

The polyester solution P introduced into the first reaction unit 16A from the inlet port 16C moves toward the second direction D2 on a surface of the filling material of the first reaction unit 16A. In contrast, the reaction solvent M in the supercritical state or the subcritical state (the pressurized gas or the pressurized liquid) introduced from the inlet port 16D moves toward the first direction D1 in the first reaction unit 16A. In the first reaction unit 16A, the reaction solvent M in the supercritical state or the subcritical state (the pressurized gas or the pressurized liquid) contacts the polyester solution P. The polyester in the polyester solution P is depolymerized (reduced in molecular weight) by the reaction solvent M, and the depolymerized polyester is extracted into the reaction solvent M in the supercritical state or the subcritical state (the pressurized gas or the pressurized liquid). Hereinafter, the polyester depolymerized in the first reaction unit 16A is referred to as a first depolymerized polyester P1, and a mixture of the first depolymerized polyester P1 and the reaction solvent M (the reaction solvent M into which the first depolymerized polyester P1 is extracted) is referred to as a first solvent M1. The first solvent M1 containing the first depolymerized polyester P1 travels through the first reaction unit 16A toward the first direction D1, and is led out to the first direction D1 side of the first reaction unit 16A.

The first depolymerized polyester P1 contains the monomers D and E that have been generated by the depolymerization of the polyester in the polyester solution P, the monomer D that has been originally mixed in the polyester solution P, and oligomers that have been generated by the depolymerization of the polyester. Herein, the oligomers can be said to be oligomers of carboxylic acid or alcohol that are not monomerized, but are depolymerized from the polyester (oligomers of carboxylic acid or alcohol having a molecular weight smaller than that of polyester). The oligomers contained in the residual substances R in the polyester solution P are also depolymerized by the reaction solvent M. Therefore, the first depolymerized polyester P1 also contains the depolymerized residual substances R. The depolymerized residual substances R include, for example, the oligomers that have been contained in the residual substances R and depolymerized, and the monomers D and E generated by depolymerizing the oligomers contained in the residual substances R.

Second Reaction Unit

The second reaction unit 16B is formed in the reaction unit 16, and the second reaction unit 16B is formed at a portion where the first solvent M1 is led out from the first reaction unit 16A. In the present embodiment, since the first solvent M1 is led out toward the first direction D1, the second reaction unit 16B can be said to be a space formed on the first direction D1 side of the first reaction unit 16A.

In the second reaction unit 16B, the first depolymerized polyester P1 contained in the first solvent M1 is further depolymerized (reduced in molecular weight) by the reaction solvent M contained in the first solvent M1. Hereinafter, the first depolymerized polyester P1 that has been further depolymerized in the second reaction unit 16B is referred to as a second depolymerized polyester P2, and a mixture of the second depolymerized polyester P2 and the reaction solvent M (reaction solvent M containing a second depolymerized polyester PE) is referred to as a second solvent M2. An outlet pipe 16*a* is connected to the second reaction unit 16B. In more detail, an outlet port 16E that is an opening of the outlet pipe 16*a* through which the second solvent M2 is led out from the second reaction unit 16B is connected to the second reaction unit 16B. The second solvent M2 containing the second depolymerized polyester P2 in the second reaction unit 16B is led out of the second reaction unit 16B from the outlet port 16E through the outlet pipe 16*a*.

The second depolymerized polyester P2 contains the monomers D and E generated by the depolymerization of the oligomers in the first depolymerized polyester P1, and the oligomers generated by the depolymerization of the first depolymerized polyester P1.

A discharge pipe 16*b* is connected to the bottom of the reaction unit 16. In more detail, a discharge port 16F that is an opening of the discharge pipe 16*b* through which non-extractables (to be described later) in the reaction unit 16 are discharged is connected to the bottom of the reaction unit 16. The non-extractables including, for example, impurities such as metal compounds that have not been extracted into the reaction solvent M and residues of undecomposed polyester that have not been extracted into the reaction solvent M are discharged from the discharge pipe 16*b*. That is, the non-extractables at the bottom of the reaction unit 16 is discharged out of the reaction unit 16 from the discharge port 16F through the discharge pipe 16*b*. The non-extractables discharged from the discharge pipe 16*b* can be said to be components of the polyester solution P that have remained in the first reaction unit 16A and the second reaction unit 16B without being led out as the second solvent M2 (reaction solvent M containing the second depolymerized polyester P2) to the separation unit 18.

The reaction unit 16 may be provided with a heating unit to heat the inside of the reaction unit 16 and a pressurizing unit to keep the pressure inside the reaction unit 16 at a predetermined value or higher. The temperature inside the reaction unit 16 is preferably 250° C. to 400° C., more preferably 250° C. to 350° C. The pressure inside the reaction unit 16 is preferably 1 MPa to 30 MPa, more preferably 6 MPa to 25 MPa. The pressurizing unit and the heating unit may be controlled by the control unit 20.

Separation Unit

The second solvent M2 containing the second depolymerized polyester P2 is introduced into the separation unit 18, and the second solvent M2 is divided into the reaction solvent M, the carboxylic acid-derived monomer D contained in the second depolymerized polyester P2, the alcohol component monomer E contained in the second depolymerized polyester P2, and the residual substances R. The residual substances R are components of the second solvent M2 other than the reaction solvent M, the monomer D, and the monomer E, and contain the oligomers.

In the present embodiment, the separation unit 18 includes a first separation unit 18A, a second separation unit 18B, and a third separation unit 18C.

The first separation unit 18A is a separation tower connected to the outlet pipe 16*a*. The second solvent M2 containing the second depolymerized polyester P2 is introduced into the first separation unit 18A through the outlet pipe 16*a*. The first separation unit 18A separates the second solvent M2 into a low boiling point component and a high boiling point component having a boiling point higher than that of the low boiling point component. For example, in the first separation unit 18A, a gaseous component may be separated as the low boiling point component, and the liquid component may be separated as the high boiling point component while setting the temperature of the second solvent M2 to a predetermined temperature. Outlet pipes 18Aa and 18Ab are connected to the first separation unit 18A. The low boiling point component is led out from the outlet pipe 18Aa, and the high boiling point component is led out from the outlet pipe 18Ab.

The second separation unit 18B is a separation tower connected to the first separation unit 18A through the outlet pipe 18Aa. The low boiling point component is introduced into the second separation unit 18B through the outlet pipe 18Aa. The second separation unit 18B separates the low boiling point component into the reaction solvent M and the monomer E. Outlet pipes 18Ba and 18Bb are connected to the second separation unit 18B. The reaction solvent M is led out from the outlet pipe 18Ba, and the monomer E is led out from the outlet pipe 18Bb. The outlet pipe 18Ba is connected to the second separation unit 18B and the solvent storage unit 14. Accordingly, the reaction solvent M led out from the second separation unit 18B is returned to the solvent storage unit 14 and reused for monomerizing the polyester.

The third separation unit 18C is a separation tower connected to the first separation unit 18A through the outlet pipe 18Ab. The high boiling point component is introduced into the third separation unit 18C through the outlet pipe 18Ab. The third separation unit 18C separates the high boiling point component into the residual substances R having a still higher boiling point, the low boiling point component including the reaction solvent M and the monomer E, and the monomer D. Outlet pipes 18Ca, 18Cb, and 18Cc are connected to the third separation unit 18C. The outlet pipe 18Ca is connected to the second separation unit 18B. The low boiling point component separated in the third separation unit 18C is led out to the second separation unit 18B through the outlet pipe 18Ca. The monomer D separated in the third separation unit 18C is led out from the outlet pipe 18Cb, and the residual substances R separated in the third separation unit 18C is led out from the outlet pipe 18Cc.

An inlet pipe 18Cd is connected to the third separation unit 18C. The inlet pipe 18Cd is connected also to the dissolving unit 12, and introduces the monomer D led out from the third separation unit 18C into the dissolving unit 12. In the example of FIG. 2, the inlet pipe 18Cd branches from the outlet pipe 18Cb. The inlet pipe 18Cd is provided with an adjusting unit 18Ce to adjust the amount of the monomer D supplied from the third separation unit 18C to the dissolving unit 12. The adjusting unit 18Ce is, for example, an on-off valve that supplies, when being open, the monomer D to the dissolving unit 12, and stops, when being closed, supplying the monomer D to the dissolving unit 12. The adjusting unit 18Ce is, however, not limited to being an on-off valve, but may be any mechanism capable of adjusting the supply of the monomer D to the dissolving unit 12. Although, in the present embodiment, the adjusting unit 18Ce is provided at a location where the inlet pipe 18Cd branches from the outlet pipes 18Cb, the location where the adjusting unit 18Ce is provided is not limited to that location, but may be any location. The inlet pipe 18Cd need not be connected to the outlet pipe 18Cb, but may be directly connected to the third separation unit 18C. For example, the outlet pipe 18Cb may be provided with a storage unit (tank) to store the monomer D, and the inlet pipe 18Cd may be connected to the storage unit.

An inlet pipe 18Cf is connected to the third separation unit 18C. The inlet pipe 18Cf is connected also to the dissolving unit 12, and introduces the residual substances R led out from the third separation unit 18C into the dissolving unit 12. In the example of FIG. 2, the inlet pipe 18Cf branches from the outlet pipe 18Cc. The inlet pipe 18Cf is provided with an adjusting unit 18Cg to adjust the amount of the residual substances R supplied from the third separation unit 18C to the dissolving unit 12. The adjusting unit 18Cg is, for example, an on-off valve that supplies, when being open, the residual substances R to the dissolving unit 12, and stops, when being closed, supplying the residual substances R to the dissolving unit 12. The adjusting unit 18Cg is, however, not limited to being an on-off valve, but may be any mechanism capable of adjusting the supply of the residual substances R to the dissolving unit 12. Although, in the present embodiment, the adjusting unit 18Cg is provided at a location where the inlet pipe 18Cf branches from the outlet pipes 18Cc, the location where the adjusting unit 18Ce is provided is not limited to that location, but may be any location. The inlet pipe 18Cf need not be connected to the outlet pipe 18Cc, but may be directly connected to the third separation unit 18C.

For example, the outlet pipe 18Cc may be provided with a storage unit (tank) to store the residual substances R, and the inlet pipe 18Cf may be connected to the storage unit. The inlet pipe 18Cf may be provided with a filter that collects foreign matter in the residual substances R while allowing passage of the oligomers in the residual substances R.

In the example of FIG. 2, the inlet pipes 10*a*, 18Cd, and 18Cf connected to the dissolving unit 12 are directly connected to the dissolving unit 12 without being connected to one another. However, at least two of the inlet pipes 10*a*, 18Cd, and 18Cf may be connected (converged), and the connected pipe may be connected to the dissolving unit 12.

Control Unit

The control unit 20 is a control device to control the monomer production system 1. The control unit 20 controls the adjusting unit 10*b* to control the amount of the polyester raw material Pm supplied from the storage unit 10 to the dissolving unit 12. The control unit 20 controls the supply unit 12*b* to control the amount of the polyester solution P supplied from the dissolving unit 12 to the first reaction unit 16A. The control unit 20 controls the heating unit 12*c* to control the degree of heating of the polyester solution P. The control unit 20 controls the heating/pressurizing unit 14*b* to bring the reaction solvent M into the supercritical state or the subcritical state (the pressurized gas or the pressurized liquid), and controls the amount of the reaction solvent M in the supercritical state or the subcritical state (the pressurized gas or the pressurized liquid) supplied to the reaction unit 16. The control unit 20 controls the adjusting unit 18Ce to control the amount of the monomer D supplied to the dissolving unit 12. The control unit 20 controls the adjusting unit 18Cg to control the amount of the residual substances R supplied to the dissolving unit 12.

The control unit 20 is a computer in the present embodiment, and includes a processor including an arithmetic circuit such as a central processing unit (CPU) and a storage unit to store therein various types of information such as details of arithmetic operations performed by the processor and computer programs. The control unit 20 performs control of the monomer production system 1 by reading the computer programs from the storage unit.

However, the monomer production system 1 is not limited to being automatically controlled by the control unit 20, and for example, at least a portion of the processing may be controlled by an operation of an operator.

Operation of Monomer Production System

The following describes an operation of the monomer production system 1. The control unit 20 controls the adjusting units 10*b*, 18Ce, and 18Cg to introduce the polyester raw material Pm, the monomer D, and the residual substances R into the dissolving unit 12, and thus mixes the polyester raw material Pm with the monomer D and the residual substances R in the dissolving unit 12 to generate the polyester solution P. The control unit 20 preferably introduces the polyester raw material Pm into the dissolving unit 12 after introducing the monomer D and the residual substances R into the dissolving unit 12. By introducing the polyester raw material Pm later, the polyester raw material Pm can be appropriately dissolved.

The control unit 20 preferably sets the ratio by weight of the total amount of the monomer D and the residual substances R supplied to the dissolving unit 12 to the amount of the polyester raw material Pm supplied to the dissolving unit 12 to 0.05 to 5, more preferably 0.1 to 2, and still more preferably 0.2 to 1. By setting the ratio of the amount of supply within the range mentioned above, the monomers D and E can be sufficiently recovered from the polyester raw material Pm while restraining a reduction in fluidity due to an excessive amount of the polyester raw material Pm. The control unit 20 preferably sets the ratio by weight of the amount of the residual substances R supplied to the dissolving unit 12 to the amount of the monomer D supplied to the dissolving unit 12 to 0 to 5, more preferably 0 to 3, and still more preferably 0.5 to 2. By setting the ratio of the amount of supply within the range mentioned above, the monomers D and E can be sufficiently recovered from the residual substances R while restraining a reduction in fluidity due to a too small amount of the monomer D.

In the present embodiment, the control unit 20 introduces a portion of the monomer D led out from the third separation unit 18C into the dissolving unit 12, and a portion of the residual substances R led out from the third separation unit 18C into the dissolving unit 12. The ratio by weight of the amount of the residual substances R introduced into the dissolving unit 12 to the amount of the residual substances R led out from the third separation unit 18C is preferably 30% to 99%, more preferably 60% to 98%. By returning the residual substances R at such a ratio, the concentration of impurities other than the oligomers in the residual substances R can be restrained from becoming too high while improving the yield of the monomers by depolymerizing the oligomers contained in the residual substances R.

The control unit 20 controls the supply unit 12*b* and the heating unit 12*c* to supply the polyester solution P to the first reaction unit 16A while heating the polyester solution P in the dissolving unit 12. The control unit 20 sets the temperature of the polyester solution P preferably to 250° C. to 400° C., more preferably to 250° C. to 350° C.

The control unit 20 controls the heating/pressurizing unit 14*b* to supply the reaction solvent M brought into the supercritical state or the subcritical state (the pressurized gas or the pressurized liquid) to the reaction unit 16. The control unit 20 sets the temperature of the reaction solvent M preferably to 250° ° C. to 400° C., more preferably to 250° C. to 350° C. The control unit 20 sets the pressure of the reaction solvent M to preferably 1 MPa to 30 MPa, more preferably to 6 MPa to 25 MPa.

By supplying the polyester solution P and the reaction solvent M to the reaction unit 16 as described above, the polyester and the oligomers contained in the polyester raw material Pm are depolymerized in the first reaction unit 16A to generate the first depolymerized polyester P1. Then, in the second reaction unit 16B, the first depolymerized polyester P1 is further depolymerized to generate the second solvent M2 that is the mixture of the second depolymerized polyester P2 and the reaction solvent M. The second solvent M2 is separated into the reaction solvent M, the monomers D and E, and the residual substances R in the first, the second, and the third separation units 18A, 18B, and 18C. Thus, the monomers D and E are recovered from the polyester raw material Pm and polymerized to regenerate the polyester raw material Pm.

Figure 3:
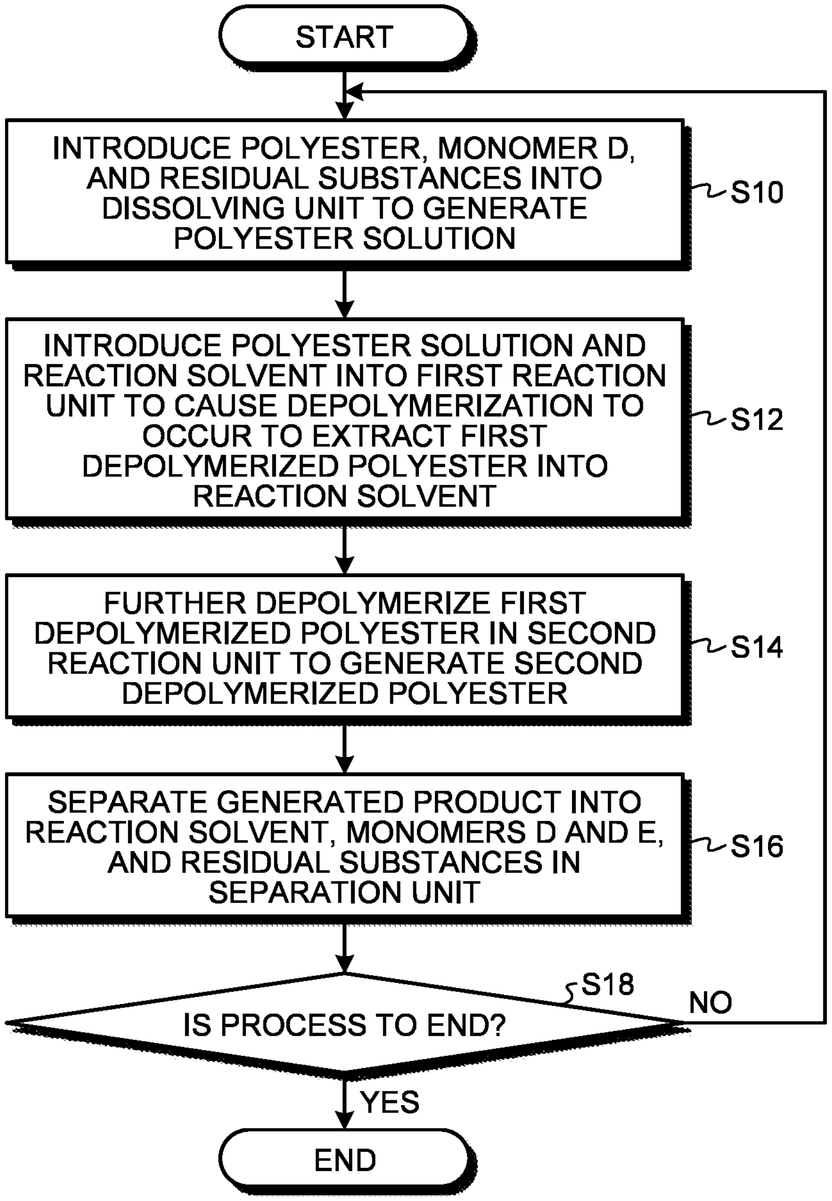
FIG. 3 is a flowchart explaining an operation flow of the monomer production system.

An operation flow of the monomer production system 1 described above will be described based on a flowchart. FIG. 3 is the flowchart explaining the operation flow of the monomer production system. As illustrated in FIG. 3, the control unit 20 introduces the polyester raw material Pm, the monomer D, and the residual substances R into the dissolving unit 12 to generate the polyester solution P (Step S10). The control unit 20 then introduces the polyester solution P and the reaction solvent M into the first reaction unit 16A to cause the depolymerization to occur to extract the first depolymerized polyester P1 into the reaction solvent M (Step S12). Then, the first solvent M1 into which the first depolymerized polyester P1 has been extracted is introduced into the second reaction unit 16B, and the first depolymerized polyester P1 is further depolymerized in the second reaction unit 16B to generate the second depolymerized polyester P2 (Step S14). Then, the second solvent M2 in which the second depolymerized polyester P2 is dissolved is separated into the reaction solvent M, the monomers D and E, and the residual substances R in the separation unit 18 (Step S16). Thereafter, if the process is to end (Yes at Step S18), this process ends, or if the process is not to end (No at Step S18), the process returns to Step S10 and continues to be executed by introducing a portion of the monomer D and the residual substances R separated in the separation unit 18 into the dissolving unit 12.

Effects

When generating the monomers D and E by depolymerizing the polyester raw material Pm, the yield of the monomers D and E is required to be improved. To solve that problem, in the present embodiment, the residual substances R that are substances other than the reaction solvent M and the monomers D and E separated in the separation unit 18 are returned to the dissolving unit 12. Since the residual substances R contain the oligomers that have not been depolymerized to the monomers, the residual substances R are returned to the dissolving unit 12 so that the oligomers contained in the residual substances R are depolymerized again to be capable of improving the yield of the monomers D and E.

Since the residual substances R are contained in the polyester solution P, the fluidity is considered to be lower than that when only the monomer D and the polyester raw material Pm are contained. As a result, the lower fluidity of the polyester solution P in the first reaction unit 16A may lower the reactivity. To solve that problem, in the present embodiment, the ratio of the amount of the residual substances R supplied to the dissolving unit 12 to the amount of the monomer D supplied to the dissolving unit 12 is specified. Therefore, according to the present embodiment, the lowering of the reactivity (depolymerization property) can be restrained when the residual substances R are added.

Figure 4:
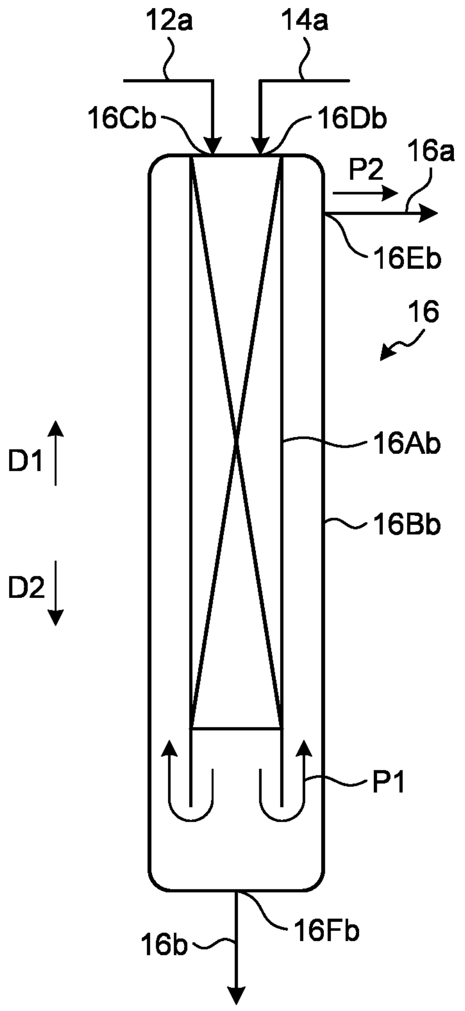
FIG. 4 is a schematic diagram illustrating another example of a reaction unit.

However, the polyester solution P and the reaction solvent M are not limited to being supplied in the directions toward each other, but may be supplied in the same direction as each other. FIG. 4 is a schematic diagram illustrating another example of the reaction unit. In this case, for example, as illustrated in FIG. 4, the reaction unit 16 may have a double-pipe structure, with an inner pipe portion serving as a first reaction unit 16Ab and an outer pipe portion serving as a second reaction unit 16Bb. In this case, an inlet port 16Cb for the polyester solution P and an inlet port 16Db for the reaction solvent M open toward the second direction D2 and connected to a surface on the first direction D1 side of the first reaction unit 16Ab. As a result, the polyester solution P and the reaction solvent M are supplied toward the second direction D2, that is, toward the same direction. The polyester solution P and the reaction solvent M travel toward the second direction D2 while reacting in the first reaction unit 16Ab, flow as the first solvent M1 (reaction solvent M into which the first depolymerized polyester P1 has been extracted) into the second reaction unit 16Bb at the distal end of the first reaction unit 16Ab, continue to further react, and are led out as the second solvent M2 (reaction solvent M containing the second depolymerized polyester P2) from an outlet port 16Eb that opens at a side of the second reaction unit 16Bb. The non-extractables are discharged from a discharge port 16Fb that opens at the bottom of the reaction unit 16.

Second Embodiment

The following describes a second embodiment of the present invention. The second embodiment differs from the first embodiment in that a plurality of the dissolving units 12 are provided. In the second embodiment, portions having the same configurations as those in the first embodiment will not be described.

Figure 5:
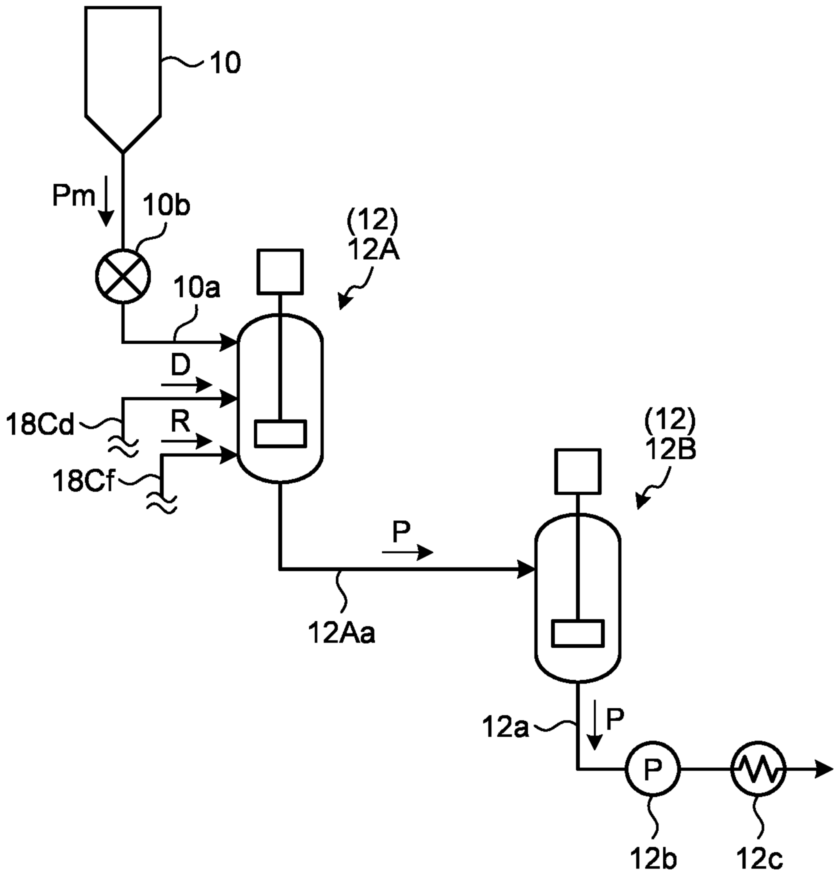
FIG. 5 is a schematic diagram of dissolving units according to a second embodiment of the present invention.

FIG. 5 is a schematic diagram of the dissolving units according to the second embodiment. As illustrated in FIG. 5, in the second embodiment, a first dissolving unit 12A and a second dissolving unit 12B are provided as the dissolving units 12. In the example of FIG. 5, the two first and second dissolving units 12A and 12B are provided, but the number of the dissolving units 12 is not limited to two, and may be three or more.

The first dissolving unit 12A is a tank into which the polyester raw material Pm, the monomer D, and the residual substances R are introduced to produce the polyester solution P. The first dissolving unit 12A is connected to the storage unit 10 through the inlet pipe 10*a*, and the polyester raw material Pm is introduced from the storage unit 10. The first dissolving unit 12A is connected to the third separation unit 18C through the inlet pipe 18Cd, and the monomer D is introduced from the third separation unit 18C. The first dissolving unit 12A is connected to the third separation unit 18C through the inlet pipe 18Cf, and the residual substances R are introduced from the third separation unit 18C.

The second dissolving unit 12B is connected to the first dissolving unit 12A through a pipe 12Aa, through which the polyester solution P generated in the first dissolving unit 12A is introduced. The second dissolving unit 12B is connected to the first reaction unit 16A through the inlet pipe 12*a*. The polyester solution P introduced into the second dissolving unit 12B is led out to the first reaction unit 16A through the inlet pipe 12*a*. Thus, in the example of FIG. 5, the second dissolving unit 12B is provided between the first dissolving unit 12A and the first reaction unit 16A, and the first dissolving unit 12A can be said to be connected in series to the second dissolving unit 12B. When three or more of the dissolving units 12 are provided, the other dissolving unit or units 12 is or are connected in series between the second dissolving unit 12B and the first reaction unit 16A, in other words, all the dissolving units 12 are connected in series. Thus, by providing the multiple dissolving units 12 and connecting them in series, the polyester solution P generated in the first dissolving unit 12A can be temporarily stored in the second dissolving unit 12B serving as a buffer tank.

Therefore, the polyester raw material Pm can be reliably dissolved and introduced into the first reaction unit 16A.

Figure 6:
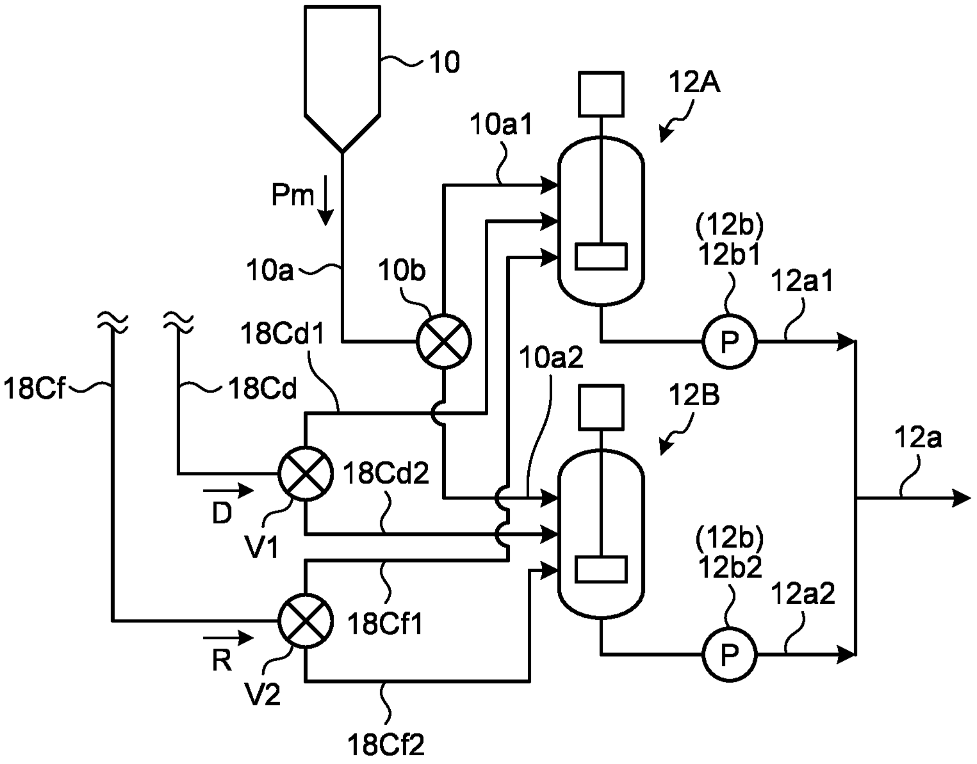
FIG. 6 is a schematic diagram of the dissolving units according to another example of the second embodiment.

However, the dissolving units 12 are not limited to being connected in series, and may be connected in parallel. FIG. 6 is a schematic diagram of the dissolving units according to another example of the second embodiment. As illustrated in FIG. 6, when the dissolving units 12 are connected in parallel, the polyester raw material Pm, the monomer D, and the residual substances R are introduced into the first and the second dissolving units 12A and 12B, and the polyester solution P is generated in the first and the second dissolving units 12A and 12B. The first and the second dissolving units 12A and 12B are connected to the first reaction unit 16A through the inlet pipe 12*a*, and the polyester solution P in the first and the second dissolving units 12A and 12B flows through the inlet pipe 12*a* and is led out to the first reaction unit 16A.

In the case of the parallel connection as illustrated in FIG. 6, the operation is preferably alternately switched between the generation of the polyester solution P and the supply of the polyester solution P to the first reaction unit 16A for each of the dissolving units 12. That is, for example, during a period when the polyester raw material Pm, the monomer D, and the residual substances R are being introduced into the first dissolving unit 12A, the polyester solution P has already been stored in the second dissolving unit 12B, and is led out from the second dissolving unit 12B to the first reaction unit 16A. During a period when the polyester raw material Pm, the monomer D, and the residual substances R are being introduced into the second dissolving unit 12B, the polyester solution P has already been stored in the first dissolving unit 12A, and is led out from the first dissolving unit 12A to the first reaction unit 16A.

Specifically, in the example of FIG. 6, the first dissolving unit 12A is connected to an inlet pipe 10*a*1 branching from the inlet pipe 10*a*, and the second dissolving unit 12B is connected to an inlet pipe 10*a*2 branching from the inlet pipe 10*a*. In the example of FIG. 6, the adjusting unit 10*b* is provided at a location where the inlet pipes 10*a*1 and 10*a*2 branch, and adjusts the amount of the polyester raw material Pm supplied from the storage unit 10 to the first dissolving unit 12A and the amount of the polyester raw material Pm supplied from the storage unit 10 to the second dissolving unit 12B. The first dissolving unit 12A is connected to an inlet pipe 18Cd1 branching from the inlet pipe 18Cd, and the second dissolving unit 12B is connected to an inlet pipe 18Cd2 branching from the inlet pipe 18Cd. In the example of FIG. 6, an adjusting unit V1 is provided at a location where the inlet pipes 18Cd1 and 18Cd2 branch. The adjusting unit V1 adjusts the amount of the monomer D supplied from the third separation unit 18C to the first dissolving unit 12A and the amount of the monomer D supplied from the third separation unit 18C to the second dissolving unit 12B. The first dissolving unit 12A is connected to an inlet pipe 18Cf1 branching from the inlet pipe 18Cf, and the second dissolving unit 12B is connected to an inlet pipe 18Cf2 branching from the inlet pipe 18Cf. In the example of FIG. 6, an adjusting unit V2 is provided at a location where the inlet pipes 18Cf1 and 18Cf2 branch. The adjusting unit V2 adjusts the amount of the residual substances R supplied from the third separation unit 18C to the first dissolving unit 12A and the amount of the residual substances R supplied from the third separation unit 18C to the second dissolving unit 12B. The first dissolving unit 12A is connected to an inlet pipe 12*a*1 that joins the inlet pipe 12*a*, and the second dissolving unit 12B is connected to an inlet pipe 12*a*2 that joins the inlet pipe 12*a*. The inlet pipe 12*a*1 is provided with a supply unit 12*b*1 to control the supply of the polyester solution P from the first dissolving unit 12A, and the inlet pipe 12*a*2 is provided with a supply unit 12*b*2 to control the supply of the polyester solution P from the second dissolving unit 12B.

During a period to generate the polyester solution P in the first dissolving unit 12A, the control unit 20 controls the supply units 12*b*1 and 12*b*2 to supply the polyester solution P from the second dissolving unit 12B to the first reaction unit 16A while controlling the adjusting units 10*b*, V1, and V2 to supply the polyester raw material Pm, the monomer D, and the residual substances R to the first dissolving unit 12A to generate the polyester solution P in the first dissolving unit 12A. During this period, the control unit 20 does not supply the polyester raw material Pm, the monomer D, and the residual substances R to the second dissolving unit 12B, and does not supply the polyester solution P from the first dissolving unit 12A to the first reaction unit 16A. In contrast, during a period to generate the polyester solution P in the second dissolving unit 12B, the control unit 20 controls the supply units 12*b*1 and 12*b*2 to supply the polyester solution P from the first dissolving unit 12A to the first reaction unit 16A while controlling the adjusting units 10*b*, V1, and V2 to supply the polyester raw material Pm, the monomer D, and the residual substances R to the second dissolving unit 12B to generate the polyester solution P in the second dissolving unit 12B. During this period, the control unit 20 does not supply the polyester raw material Pm, the monomer D, and the residual substances R to the first dissolving unit 12A, and does not supply the polyester solution P from the second dissolving unit 12B to the first reaction unit 16A. The configuration of FIG. 6 is exemplary, and any layout other than that of FIG. 6 may be employed as long as the dissolving units 12 are connected in parallel. The number of the dissolving units 12 may be three or more also when the dissolving units 12 are connected in parallel.

As described above, in the second embodiment, the dissolving units 12 are connected in series or in parallel, but the series connection may be combined with the parallel connection. That is, for example, other of the dissolving units 12 may be connected in series to the dissolving units 12 connected in parallel.

Third Embodiment

The following describes a third embodiment of the present invention. The third embodiment differs from the first embodiment in that the non-extractables discharged from the reaction unit 16 are also mixed with the polyester solution P. In the third embodiment, portions having the same configurations as those in the first embodiment will not be described. The third embodiment is also applicable to the second embodiment.

Figure 7:
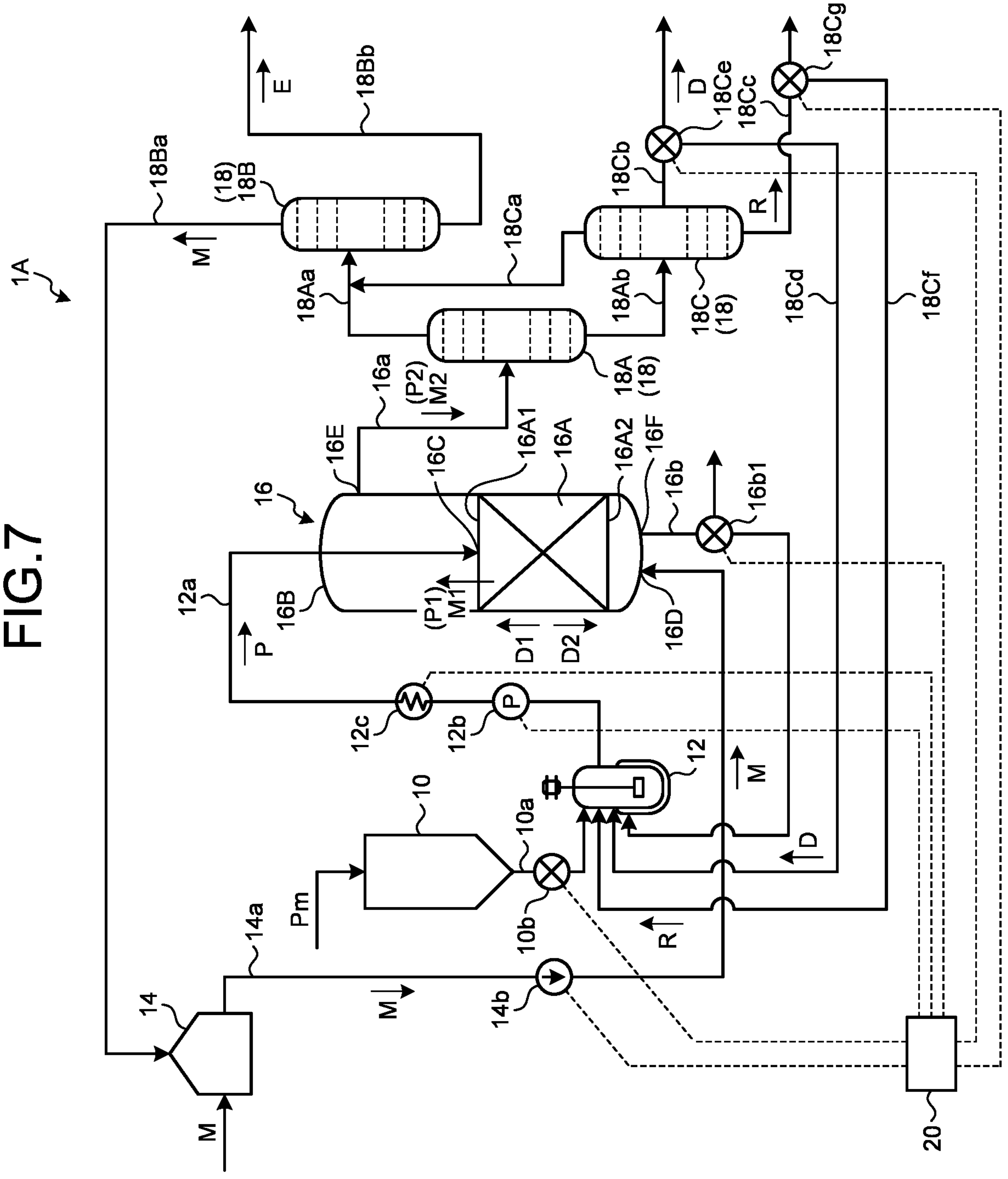
FIG. 7 is a schematic diagram of a monomer production system according to a third embodiment of the present invention.

FIG. 7 is a schematic diagram of a monomer production system according to the third embodiment. As illustrated in FIG. 7, in a monomer production system 1A according to the third embodiment, the discharge pipe 16*b* connected to the bottom of the reaction unit 16 is connected to the dissolving unit 12. The non-extractables in the reaction unit 16 is supplied to the dissolving unit 12 through the discharge pipe 16*b*. In more detail, the discharge pipe 16*b* is provided with an adjusting unit 16*b*1 to adjust the amount of the non-extractables supplied to the dissolving unit 12. The adjusting unit 16*b*1 is, for example, an on-off valve that supplies, when being open, the non-extractables in the reaction unit 16 to the dissolving unit 12, and stops, when being closed, supplying the non-extractables in the reaction unit 16 to the dissolving unit 12. In the third embodiment, the control unit 20 controls the adjusting unit **16*b*1 to control the supply of the non-extractables in the reaction unit 16 to the dissolving unit 12. The timing of discharging the non-extractables from the reaction unit 16 may be any timing. For example, the level of the non-extractables may be controlled so as to fall within a predetermined range using a level meter provided at the bottom of the reaction unit 16, or the non-extractables may be periodically discharged at constant time intervals. The level meter herein may detect a difference in density between the reaction solvent M and the non-extractables. The adjusting unit 16*b*1 is not limited to being an on-off valve, but may be any mechanism capable of adjusting the supply of the non-extractables to the dissolving unit 12**.

Since the oligomers contained in the non-extractables can be monomerized by returning the non-extractables to the dissolving unit 12 as in the third embodiment, the yield of the monomers can be further improved.

Effects of Present Disclosure

As described above, the monomer production system 1 according to the present disclosure includes the dissolving unit 12, the first reaction unit 16A, the second reaction unit 16B, the separation unit 18, and the inlet pipes 18Cd and 18Cf. The dissolving unit 12 stores therein the polyester solution P in which the polyester is dissolved in the carboxylic acid-derived monomer D. The polyester solution P and the reaction solvent M that reacts with the polyester are introduced into the first reaction unit 16A, which in turn brings the polyester solution P into contact with the reaction solvent M to depolymerize the polyester in the polyester solution P and extract the first depolymerized polyester P1 containing the depolymerized polyester into the reaction solvent M. The reaction solvent M (first solvent M1) into which the first depolymerized polyester P1 has been extracted is introduced into the second reaction unit 16B, which in turn causes the first depolymerized polyester P1 to further react with the reaction solvent M to further depolymerize the first depolymerized polyester P1 and generate the second depolymerized polyester P2 that is the further depolymerized first depolymerized polyester P1. The reaction solvent M in which the second depolymerized polyester P2 is dissolved (second solvent M2) is introduced into the separation unit 18, which in turn separates the reaction solvent M in which the second depolymerized polyester P2 is dissolved into the reaction solvent M, the carboxylic acid-derived monomer D contained in the second depolymerized polyester P2, the alcohol component monomer E contained in the second depolymerized polyester P2, and the residual substances R that are the components other than the reaction solvent M, the carboxylic acid-derived monomer D, and the alcohol component monomer E, and contain the oligomers. The inlet pipes 18Cd and 18Cf introduce the carboxylic acid-derived monomer D and the residual substances R into the dissolving unit 12.

When generating the monomers D and E by depolymerizing the polyester raw material Pm, the yield of the monomers D and E is required to be improved. To solve that problem, in the present embodiment, the residual substances R separated in the separation unit 18 are returned to the dissolving unit 12. Since the residual substances R contain the oligomers that have not been depolymerized to the monomers, the residual substances R are returned to the dissolving unit 12 so that the oligomers contained in the residual substances R are depolymerized again to be capable of improving the yield of the monomers D and E.

The inlet pipes 18Cd and 18Cf preferably introduce a part of the carboxylic acid-derived monomer D separated in the separation unit 18 and a part of the residual substances R separated in the separation unit 18 into the dissolving unit 12. According to the monomer production system 1, since a part of the monomer D is returned to the dissolving unit 12, the yield of the monomer D can be restrained from decreasing while improving the fluidity of the polyester raw material Pm by the monomer D. According to the monomer production system 1, since a part of residual substances R is returned to the dissolving unit 12, the concentration of the impurities contained in the residual substances R can be restrained from increasing while improving the yield of the monomers D and E.

The monomer production system 1 further includes the control unit 20 that controls the supply of the polyester raw material Pm, the carboxylic acid-derived monomer D, and the residual substances R to the dissolving unit 12. The control unit 20 preferably introduces the polyester raw material Pm into the dissolving unit 12 after the carboxylic acid-derived monomer D and the residual substances R have been introduced into the dissolving unit 12. According to the monomer production system 1, by introducing the polyester raw material Pm later, the polyester raw material Pm can be restrained from being defectively dissolved.

The monomer production system 1 further includes the control unit 20 that controls the supply of the polyester raw material Pm, the carboxylic acid-derived monomer D, and the residual substances R to the dissolving unit 12. The control unit 20 preferably sets the weight ratio of the total supply amount of the carboxylic acid-derived monomer D and the residual substances R to the supply amount of the polyester raw material Pm to 0.05 to 5. By setting the mixing ratio of the polyester raw material Pm, the monomer D, and the residual substances R within this range, the monomers D and E can be sufficiently recovered from the polyester raw material Pm while restraining the decrease in fluidity due to a too large amount of the polyester raw material Pm.

The control unit 20 preferably sets the weight ratio of the supply amount of the residual substances R to that of the carboxylic acid-derived monomer D to 0 to 5. By setting the ratio of the supply amount of the residual substances R within this range, the monomers D and E can be sufficiently recovered from the residual substances R while restraining the decrease in fluidity due to a too small amount of the monomer D. The monomers D and E can be sufficiently recovered from the residual substances R while restraining the decrease in fluidity due to a too small amount of the monomer D.

The monomer production system 1 is preferably provided with a plurality of the dissolving units 12. By providing the multiple dissolving units 12, the dissolving unit that dissolves the polyester raw material Pm can be separated from the dissolving unit that supplies the polyester solution P to the first reaction unit 16A. Therefore, the raw material of the polyester solution P need not be supplied while being controlled to achieve a desired mixing ratio, but the desired mixing ratio only needs to be finally achieved. In addition, since the time for dissolving the polyester raw material Pm can be ensured, troubles caused by the undissolved polyester raw material Pm (such as pipe blockages) can be reduced.

The monomer production system 1 preferably includes the first dissolving unit 12A into which the polyester, the carboxylic acid-derived monomer D, and the residual substances R are introduced to generate the polyester solution P, and the second dissolving unit 12B into which the polyester solution P generated in the first dissolving unit 12A is introduced to lead out the introduced polyester solution P to the first reaction unit 16A. By connecting the multiple dissolving units 12 in series in this way, the polyester raw material Pm can be reliably dissolved and introduced into the first reaction unit 16A.

The monomer production system 1 preferably includes the first dissolving unit 12A and the second dissolving unit 12B into which the polyester, the carboxylic acid-derived monomer D, and the residual substances R are introduced to generate the polyester solution P. During the period when the polyester, the carboxylic acid-derived monomer D, and the residual substances R are being introduced into the first dissolving unit 12A, the polyester solution P is led out from the second dissolving unit 12B to the first reaction unit 16A. During the period when the polyester, the carboxylic acid-derived monomer D, and the residual substances R are being introduced into the second dissolving unit 12B, the polyester solution P is led out from the first dissolving unit 12A to the first reaction unit 16A. By connecting the dissolving units 12 in parallel in this way and switching between the dissolving unit that dissolves the polyester raw material Pm and the dissolving unit that supplies the polyester solution P to the first reaction unit 16A, the polyester raw material Pm can be reliably dissolved and introduced into the first reaction unit 16A.

The polyester solution P and the reaction solvent M are preferably introduced into the first reaction unit 16A in directions toward each other.

The monomer production system 1A preferably includes the discharge pipe 16*b* that introduces the non-extractables into the dissolving unit 12. The non-extractables are components that remain in the first reaction unit 16A and the second reaction unit 16B without being led out to the separation unit 18. By returning the non-extractables to the dissolving unit 12, the yield of the monomers D and E can be further improved.

The polyester raw material Pm preferably contains polyethylene terephthalate. The reaction solvent M is preferably methanol. The carboxylic acid-derived monomer D is preferably dimethyl terephthalate. The alcohol component monomer E is preferably ethylene glycol. According to the monomer production system 1, the yield of dimethyl terephthalate and ethylene glycol can be appropriately improved.

A monomer production method of the present disclosure includes a step of generating the polyester solution P in which the polyester is dissolved in the carboxylic acid-derived monomer D in the dissolving unit 12, a step of depolymerizing the polyester in the polyester solution P and extracting the first depolymerized polyester P1 containing the depolymerized polyester into the reaction solvent M by bringing the polyester solution P into contact with the reaction solvent M, a step of further depolymerizing the first depolymerized polyester P1 and generating the second depolymerized polyester P2 that is the further depolymerized first depolymerized polyester P1 by causing the first depolymerized polyester P1 to further react with the reaction solvent M, a step of separating the reaction solvent M in which the second depolymerized polyester P2 is dissolved into the reaction solvent M, the carboxylic acid-derived monomer D contained in the second depolymerized polyester P2, the alcohol component monomer E contained in the second depolymerized polyester P2, and the residual substances R that are the components other than the reaction solvent M, the carboxylic acid-derived monomer D, and the alcohol component monomer E, and contain the oligomers, and a step of introducing the carboxylic acid-derived monomer D and the residual substances R into the dissolving unit 12. According to this method, the yield of the monomers can be improved by returning the residual substances R to the dissolving unit 12.

While the embodiments of the present invention have been described above, the embodiments are not limited to the content of the embodiments described above. The components described above include those easily conceivable by those skilled in the art, those that are substantially the same, and those in the scope of what are called equivalents. In addition, the components described above can be combined as appropriate. Furthermore, the components can be variously omitted, replaced, or modified within the scope not deviating from the gist of the embodiments described above.

REFERENCE SIGNS LIST

10 Storage unit
12 Dissolving unit
14 Solvent storage unit
16A First reaction unit
16B Second reaction unit
18 Separation unit
18A First separation unit
18B Second separation unit
18C Third separation unit
18Cd, 18Cf Inlet pipes
20 Control unit
D, E Monomers
M Reaction solvent
P Polyester solution
Pm Polyester raw material
P1 First depolymerized polyester
P2 Second depolymerized polyester
R Residual substances

The invention claimed is:

1. A monomer production system comprising:

a dissolving unit configured to store a polyester solution in which polyester is dissolved in a carboxylic acid-derived monomer;

a first reaction unit into which the polyester solution and a reaction solvent to react with the polyester are introduced to bring the polyester solution into contact with the reaction solvent to depolymerize the polyester in the polyester solution and extract a first depolymerized polyester containing the depolymerized polyester into the reaction solvent;

a second reaction unit into which the reaction solvent with the extracted first depolymerized polyester is introduced to cause the first depolymerized polyester to further react with the reaction solvent to further depolymerize the first depolymerized polyester and generate a second depolymerized polyester that is the further depolymerized first depolymerized polyester;

a separation unit into which the reaction solvent with the dissolved second depolymerized polyester is introduced to separate the reaction solvent with the dissolved second depolymerized polyester into the reaction solvent, the carboxylic acid-derived monomer contained in the second depolymerized polyester, an alcohol component monomer contained in the second depolymerized polyester, and residual substances that are components other than the reaction solvent, the carboxylic acid-derived monomer, and the alcohol component monomer, the residual substances containing oligomers; and inlet pipes configured to introduce the carboxylic acid-derived monomer and the residual substances into the dissolving unit.

2. The monomer production system according to claim 1, wherein the inlet pipes are configured to introduce a part of the carboxylic acid-derived monomer separated in the separation unit and a part of the residual substances separated in the separation unit into the dissolving unit.

3. The monomer production system according to claim 1, further comprising a control unit configured to control supply of a polyester raw material containing the polyester, the carboxylic acid-derived monomer, and the residual substances to the dissolving unit, wherein the control unit is configured to introduce the polyester raw material into the dissolving unit after the carboxylic acid-derived monomer and the residual substances are introduced into the dissolving unit.

4. The monomer production system according to claim 1, further comprising a control unit configured to control supply of a polyester raw material containing the polyester, the carboxylic acid-derived monomer, and the residual substances to the dissolving unit, wherein the control unit is configured to set a weight ratio of a total supply amount of the carboxylic acid-derived monomer and the residual substances to a supply amount of the polyester raw material to 0.05 to 5.

5. The monomer production system according to claim 4, wherein the control unit is configured to set a weight ratio of a supply amount of the residual substances to that of the carboxylic acid-derived monomer to 0 to 5.

6. The monomer production system according to claim 1, wherein a plurality of the dissolving units are provided.

7. The monomer production system according to claim 6, comprising:

a first dissolving unit into which the polyester, the carboxylic acid-derived monomer, and the residual substances are introduced to generate the polyester solution; and a second dissolving unit into which the polyester solution generated in the first dissolving unit is introduced to lead out the introduced polyester solution to the first reaction unit.

8. The monomer production system according to claim 6, comprising a first dissolving unit and a second dissolving unit into which the polyester, the carboxylic acid-derived monomer, and the residual substances are introduced to generate the polyester solution, wherein the polyester solution is configured to be led out from the second dissolving unit to the first reaction unit during a period when the polyester, the carboxylic acid-derived monomer, and the residual substances are being introduced into the first dissolving unit, and the polyester solution is configured to be led out from the first dissolving unit to the first reaction unit during a period when the polyester, the carboxylic acid-derived monomer, and the residual substances are being introduced into the second dissolving unit.

9. The monomer production system according to claim 1, wherein the polyester solution and the reaction solvent are introduced into the first reaction unit in directions toward each other.

10. The monomer production system according to claim 1, further comprising a pipe configured to introduce, into the dissolving unit, non-extractables that are components that remain in the first reaction unit and the second reaction unit without being led out to the separation unit as the reaction solvent with the dissolved second depolymerized polyester.

11. The monomer production system according to claim 1, wherein the polyester is polyethylene terephthalate, the reaction solvent is methanol, the carboxylic acid-derived monomer is dimethyl terephthalate, and the alcohol component monomer is ethylene glycol.

12. A monomer production method comprising:

generating a polyester solution in which polyester is dissolved in a carboxylic acid-derived monomer in a dissolving unit;

depolymerizing the polyester in the polyester solution and extracting a first depolymerized polyester containing the depolymerized polyester into the reaction solvent by bringing the polyester solution into contact with the reaction solvent;

further depolymerizing the first depolymerized polyester to generate a second depolymerized polyester that is the further depolymerized first depolymerized polyester by causing the first depolymerized polyester to further react with the reaction solvent;

separating the reaction solvent with the dissolved second depolymerized polyester into the reaction solvent, the carboxylic acid-derived monomer contained in the second depolymerized polyester, an alcohol component monomer contained in the second depolymerized polyester, and residual substances that are components other than the reaction solvent, the carboxylic acid-derived monomer, and the alcohol component monomer, the residual substances containing oligomers; and introducing the carboxylic acid-derived monomer and the residual substances into the dissolving unit.

* * * * *